(12) United States Patent
Einsele

(10) Patent No.: US 6,605,439 B2
(45) Date of Patent: Aug. 12, 2003

(54) EXTRACTION, AMPLIFICATION AND SEQUENTIAL HYBRIDIZATION OF FUNGAL CELL DNA AND PROCESS FOR DETECTION OF FUNGAL CELLS IN CLINICAL MATERIAL

(75) Inventor: Hermann Einsele, Tübingen (DE)

(73) Assignee: Eberhard-Karls Universität Tübingen Universitätsklinikum, Tubingen (DE)

( * ) Notice: Subject to any disclaimer, the term of this patent is extended or adjusted under 35 U.S.C. 154(b) by 0 days.

(21) Appl. No.: 09/867,372

(22) Filed: May 29, 2001

(65) Prior Publication Data
US 2002/0115077 A1 Aug. 22, 2002

Related U.S. Application Data

(63) Continuation of application No. 09/011,931, filed on Jun. 22, 1998, now abandoned.

(30) Foreign Application Priority Data

| Aug. 17, 1995 | (DE) | 195 30 333 |
| Aug. 17, 1995 | (DE) | 195 30 336 |
| Aug. 17, 1995 | (DE) | 195 30 332 |

(51) Int. Cl.[7] .......................... C12Q 1/68; C12P 19/36; C07H 21/04
(52) U.S. Cl. .................. 435/6; 435/91.2; 536/23.1; 536/24.3
(58) Field of Search ................ 435/6, 91.2; 536/23.1, 536/24.3

(56) References Cited

U.S. PATENT DOCUMENTS

| 4,130,395 A | 12/1978 | Chryssanthou |
| 5,426,026 A | 6/1995 | Jordan et al. |
| 5,426,027 A | 6/1995 | Lott et al. |
| 5,434,048 A | 7/1995 | Simon et al. |

FOREIGN PATENT DOCUMENTS

| EP | 0 285 439 A2 | 10/1988 |
| EP | 0 335 633 A2 | 10/1989 |
| EP | 0 422 869 A2 | 4/1991 |
| EP | 0 574 267 A2 | 12/1993 |
| JP | 08 089 254 A | 4/1996 |
| WO | WO92/08807 | 5/1992 |
| WO | WO93/23568 | 11/1993 |

OTHER PUBLICATIONS

Journal of Clinical Microbiology Bd. 32, Nr. 1, Jan. 1994, Holmes et al.: Detection of *Candida albicans* and Other Yeasts in Blood by PCR.

Bone Marrow Transplantation, 13 Marz 1994, Seite 184 XP000645489; Einsele H. et al: "Detection of Various Fungal Pathogens in Blood Samples by PCR".

Surgery, Aug. 1990, Buchman, et al., Detection of surgical pathogens by in vitro DNA amplification. Part I. Rapid identification of *Candida albicans* by in vitro amplification of a fungus–specific gene, vol. 108, No. 2, pp. 338–347.

*Primary Examiner*—Ethan Whisenant
*Assistant Examiner*—Joyce Tung
(74) *Attorney, Agent, or Firm*—Knobbe, Martens, Olson & Bear, LLP

(57) ABSTRACT

For the detection of fungal cells in clinical material fungal DNA is extracted from whole blood and the extracted fungal DNA is then detected. From this detection, a fungal infection can be concluded. For further diagnosis, the fungal species are then determined from the extracted fungal DNA. The method for extraction of the fungal DNA from whole blood comprises the isolation of predominantly intact fungal cells from the whole blood and the extraction of DNA from the isolated fungal cells. For detection of fungal DNA, at least one segment of the fungal DNA to be detected is amplified, then the amplification products are detected. For further identification of the fungal species, nucleotide sequence segments being characteristic for the fungal species are detected.

32 Claims, No Drawings

EXTRACTION, AMPLIFICATION AND SEQUENTIAL HYBRIDIZATION OF FUNGAL CELL DNA AND PROCESS FOR DETECTION OF FUNGAL CELLS IN CLINICAL MATERIAL

This application is a continuation of U.S. patent application Ser. No. 09/011,931. filed on Jun. 22, 1998, now abandoned, which was the U.S. National Phase under 35 U.S.C. §371 of International Application No. PCT/EP96/03580, filed Aug. 13, 1996 and published in German, which claims priority to German Application Nos. 195 30 332.6, filed Aug. 17, 1995, 195 30 333.4, filed Aug. 17, 1995 and German Application No. 195 30 336.9, filed Aug. 17, 1995.

The present invention generally relates to a process for detection of fungal cells in clinical material.

Such processes are known from practice, and are usually based on cultivation of fungal species from clinical material on adequate nutrient media.

The speed and sensitivity of identification are greatly affected by the cultivation, e.g. in Petri dishes, and detection on the basis of the colonies which have grown or not, particularly on account of the slow growth of the fungal species. An invasive fungal infection can thus often only be diagnosed by an extremely complicated biopsy of an organ or even only after the death of a patient.

The interest in a process for detection of fungal cells must be seen in relation to the fact that particularly over the past few years, fungal pathogens have become very important for immunosuppressed patients as significant nosocomial pathogens. Invasive fungal infections have increased considerably following bone marrow transplantation (BMT), though also after liver, kidney, pancreas and heart or heart-lung transplantation. In 1994, for example, there was an accumulation of infections, particularly Aspergillus infections, in French BMT centers which resulted in closure of these centers for a number of months.

Apart from patients with organ transplants, patients suffering from cancer, particularly after chemotherapy or surgery, patients with burns and patients in surgical and neonatal intensive care units are being increasingly affected by invasive fungal pathogens. As soon as an organ system or even a number of organ systems are affected in these groups of patients, the mortality rate for these infectious complications rises to between 80 and 100%.

The success of a therapy can only be improved in such cases through an early diagnosis. On account of the disadvantages associated with the standard detection methods mentioned above, there have been intensive attempts to permit an early, safe diagnosis of a systemic fungal infection.

Although new techniques based on molecular biology methods have already permitted a more sensitive diagnosis and thus partly an earlier detection and treatment of the infectious diseases for a number of other pathogens, this has as yet been impossible for fungal pathogens.

However, the publication "Detection of various fungal pathogens in blood samples" in: EBMT 1995, Vol. 15, Suppl. 2, March 1995, Abstract Book, Abstract 432, P. 103, already describes the amplification of a DNA segment of a fungal gene using the PCR method so as to identify a number of fungal pathogens in blood. Through an additional hybridization with species-specific oligonucleotides, a differentiation between various fungal strains was also possible.

The most important problems during the detection of fungal infections using molecular biology techniques are caused by the very complex composition of the fungal cell walls, which have made time-consuming and expensive extraction methods necessary until now.

A further problem is the fact that an increasing number of fungal species can trigger dangerous infections in immunosuppressed patients, leading to the necessity of the recording and detection of a whole range of different fungal species and strains in these patients. Since therapies differ for various fungal species it is necessary to not only record all fungal species but also to differentiate between and identify these species.

In view of the above, it is an object of the present invention to improve the process mentioned above to permit an early diagnosis of a fungal infection.

The process should be as quick and easy as possible, it should record as many fungal species as possible and it should also be able to identify these in a further stage of development.

The process to detect fungal pathogens in clinical material found in accordance with the invention comprises the following steps:
1.) extraction of fungal DNA from whole blood; and
2.) detection of extracted fungal DNA.

By abandoning the traditional cultivation of fungal species from clinical material and turning to the fungal DNA itself a process has been developed which permits a very early detection of fungal infections with a high sensitivity through detection of the fungal-specific DNA. Since the detection can be performed on the DNA level, at least partially highly sensitive, well established and fast processes can be used, leading to great advantages over known methods in terms of sensitivity and speed. It should be remembered that the release and purification of the fungal DNA must be performed not only quickly but also almost completely and relatively purely to guarantee a high sensitivity and permit a rapid diagnosis.

Moreover, the new process should be sensitive for a number of fungal species, and the fungal species should also be identified in the least possible procedural steps.

This further object is achieved in the aforementioned new process through the following procedural step which is carried out in addition to or in place of procedural step 2.):
3.) determination of the fungal species from the extracted fungal DNA.

This process has the further advantage that the diagnosis of the specific fungal infection on the DNA level can be carried out very quickly and displays a high specificity, since, for example, known sequencing processes can be used.

A number of problems had to be overcome in the individual steps of the new process, some of which arose from the composition of the fungal cell wall and from the fact that a large number of the fungal cells are not freely dissolved in whole blood but are located in a number of blood cell populations following phagocytosis, especially in granulocytes and macrophages.

The object of the present application is thus also the isolated first step in the process, namely the extraction of fungal DNA from whole blood. Although this process can be used advantageously in diagnostics to detect a fungal infection in a patient, it can also be employed wherever fungal DNA is required for other further processing.

Using the new process for example, fungal DNA can be extracted from the blood of animals which have been specifically infected by the fungal species in question. DNA probes can be cut out from the fungal DNA obtained in this manner which can then be used for detection reactions or be cloned in plasmids. Applications throughout the whole field of basic research, diagnostics, therapy, industrial gene technology, etc. are conceivable.

The process for the extraction of fungal DNA should be able to reliably extract fungal DNA even with very small quantities of fungi in whole blood. Furthermore, this step of the process should be able to be performed quickly and easily so that it can be employed in everyday work in hospitals by trained personnel.

This object is achieved in accordance with the invention in that the step of extracting fungal DNA from whole blood comprises the steps of:
a) isolation of predominantly intact fungal cells from whole blood; and
b) extraction of DNA from the isolated fungal cells.

The object of the invention is completely achieved in this manner. The new process now comprises two stages, comprising isolation of fungal cells from whole blood in the first step and then extracting of DNA from these isolated fungal cells in the second step so that the extracted DNA can be used to detect and if necessary identify fungal infections. This two-stage process above all improves the specificity since only small amounts of any interfering other DNA are present in the second step of the process.

It is preferred if the process comprises the following procedural steps:
a1) disintegration of the blood cells in whole blood;
a2) isolation of predominantly intact fungal cells from cellular DNA;
b1) disintegration of isolated fungal cells; and
b2) isolation of fungal DNA.

This leads to a very rapid and safe separation of fungal DNA from cellular DNA. The cellular DNA is released in this initial solution by lysis of blood cells in whole blood so that the fungal cells which up to then have not been, or at least have not been completely disintegrated by the preceding disintegration process, can be separated from the free cellular DNA in a quick and easy process, e.g. through centrifugation. During the subsequent lysis of the fungal cells isolated in this manner it can be safely assumed that there is no or only an insignificant amount of cellular DNA in the solution. The disintegration of the blood cells in step a1) must thus be carried out in such a way that the fungal cells are not yet lysed. Since the fungal cell wall is much more complex than the cell wall of blood cells this can be ensured through adequate careful disintegration processes.

The procedural step a1) has a further advantage, namely that it releases any phagocyted fungi so that very small quantities of fungi can still be extracted from the whole blood, particularly for diagnostic purposes. With the new process it is no longer necessary for at least a few fungal cells to be freely dissolved in whole blood, it is more than sufficient if a few fungal cells are present after phagocytosis, e.g. in granulocytes or macrophages.

It is preferred if the following steps are carried out in step a):
a1.1) lysis of the erythrocytes by osmotic hemolysis;
a1.2) enzymatic disintegration of the leukocytes; and
a2.1) centrifugation of the whole blood treated in this manner and use of the pellet in the next procedural steps.
The advantage here is that although the blood cells are reliably dissolved in steps a1.1) and a1.2), the fungal cells themselves are not damaged yet. The subsequent centrifugation then ensures a very safe separation between the released cellular DNA and cell fragments of the blood cells on the one hand and the still predominantly intact fungal cells on the other. This also ensures that no fungal DNA is lost since fungal DNA is still present in the fungal cells in the pellet. Summing up, the advantages of the aforementioned steps are thus that on the one hand even minimal concentrations of fungal cells can be detected and on the other the isolated fungal DNA is at most only slightly contaminated with cellular DNA, permitting a high sensitivity and specificity in the subsequent diagnostic steps since the ratio of fungal to cellular DNA has been significantly improved in favor of fungal DNA.

In a further development it is then preferred if the following steps are carried out in step b):
b1.1) alkaline lysis and enzymatic treatment of the fungal cells.

It could be shown that this simple procedural step permits a safe disintegration of the fungal cells which are recovered from the pellet in procedural step a2.1).

It is furthermore preferable if the lysis of the erythrocytes in step a1.1) is carried out using a hypotonic solution, preferably with a final concentration of approx. 10 mM Tris pH 7.6, 5 mM $MgCl_2$ and 10 mM NaCl, and if in step a1.2) the enzymatic digestion of the leukocytes is carried out in a solution having a final concentration of 200 μg/ml proteinase K, 10 mM Tris pH 7.6, 10 mM EDTA pH 8.0, 50 mM NaCl and 0.2% SDS.

In a further development the solution from step a1.2) is incubated for 100–140 min, preferably 120 min, at 60–70° C., preferably at 65° C.

It has been found that in this way the blood cells can be reliably and completely disintegrated without damaging the fungal cells so that after these procedural steps both the fungal cells freely in solution and the phagocyted fungal cells in the initial blood remain relatively undamaged and can be separated by centrifugation without losing their DNA.

It is furthermore preferable if step b1.1) comprises the following steps:
incubation of the fungal cells present in the pellet from step a2.1) at 90–98° C., preferably 95, for 5–15 min, preferably 10 min., in a solution with 50 mM NaOH,
neutralization with 1 M Tris-HCl pH 7.0,
enzymatic treatment with zymolyase for 50–70 min, preferably 60 min at 30–40° C., preferably 37° C.,
protein denaturation by incubation with Tris/EDTA at 60–70° C., preferably 65° C., for 10–30 min, preferably 20 min.

It has been found that these procedural steps permit a safe disintegration of the fungal cells with a subsequent complete release of fungal DNA so that the fungal DNA is then in solution and can be isolated from the cell fragments of the fungal cells.

It is preferred if in this connection step b2) comprises the following steps:
protein precipitation with 5 M potassium acetate, and
DNA precipitation of the supernatant in ice-cold isopropanol.

These procedural steps are very easy to be carried out, the protein is firstly precipitated by adding potassium acetate, the supernatant then removed and mixed with ice-cold isopropanol so that the DNA is precipitated. The precipitated DNA can then be used in the further procedural steps, i.e. to detect and identify a fungal infection.

Summing up the procedure as described up to now, the first advantage is that the fungal species can be generally detected on the basis of their DNA and can then be specifically identified. The fungal DNA is not extracted directly from the whole blood, rather there is firstly a separation of the fungal cells from cellular DNA to improve the sensitivity and specificity of the detection. In other words, if only very few fungal cells are present in the whole blood the very small quantity of fungal DNA extracted from this could be detected against the back-ground of cellular DNA present in a very high concentration, so that the separation mentioned above leads to great advantages in terms of sensitivity.

A further advantage of the new process is that phagocyted fungal cells are also available for detection purposes since the blood cells of the whole blood are initially disintegrated without damaging the fungal cells, irrespective of whether these are in solution or phagocyted. The fungal cells are only disintegrated following separation of the fungal cells from the cellular DNA and remaining cell debris of the blood cells. The method employed here ensures a complete disintegration with no damage to the fungal DNA despite the lightly complex fungal cell walls.

The object of the present invention is also a kit to carry out the process described above. Such a kit can contain a set of all basic solutions which are required for the aforementioned procedural steps. However, it is also possible to include in this kit only those basic solutions normally not found in a laboratory, e.g. the Tris buffer is dispensible, though at least the proteinase K and zymolyase are present in the kit.

The object of the present application is also the second step of the process, either isolated or in combination with the first step of the process described above, i.e. the detection of extracted fungal DNA. The fungal DNA to be detected is hereby preferably extracted and isolated as described above. However, it is also possible to obtain the fungal DNA by suitable density gradient centrifugation, specific precipitation steps with DNA probes, etc.

In all of these cases it is desirable to detect whether fungal DNA is actually present in that initial solution for further use.

Although the fungal DNA can be advantageously employed for the diagnosis of fungal infections, it can also be used differently. The fungal DNA can be obtained from agar plates or from the blood of animals which have been specifically infected with the fungal species in question. DNA probes can be cleaved from the fungal DNA obtained in this manner which can then be used for detection reactions or cloned in plasmids. Applications throughout the whole field of basic research, diagnostics, therapy, industrial gene technology, etc. are conceivable.

The new detection step should permit the recording of a number of various fungal species, even in low concentrations, in the initial solution in one single process so that it is possible to say whether there is a fungal infection at all very quickly and at an early stage in the diagnosis. Moreover, the new process should be able to be performed quickly and easily so that it can be employed in everyday work in hospitals by trained personnel.

The object is achieved in accordance with the invention in that the step to detect the extracted fungal DNA comprises the following steps:

c) amplification of at least a segment of the isolated fungal DNA; and
d) detection of the amplification product.

There are a number of standard methods with which even small amounts of an isolated DNA can initially be amplified and then detected. These methods are highly specific and very sensitive so that they provide the desired features for diagnosis, therapy, industrial gene technology, etc. Furthermore, these methods can be performed by trained personnel.

The amplification can be carried out either by PCR, cloning, DNA-dependent DNA-polymerases, etc., and the detection can be carried out by gel electrophoresis, optical density, staining with markers which bind specifically to nucleic acid, etc.

In a further development the amplification is carried out by means of a polymerase chain reaction (PCR) using two primers which bind to the DNA of a number of different fungal species, preferably to the fungal gene for the 18ssu-rRNA.

The advantage here is that a simple and in the meantime established method can be used to produce adequate amounts of DNA which is then easily detected, though the DNA can also further be used to identify the corresponding fungal species.

It is preferred if the nucleotide sequences SEQ ID-No: 1 and SEQ ID-No: 2 from the enclosed sequence listing are used as primers in step c).

The inventor of the present application surprisingly found that these two nucleotide sequences can be used as primers for various clinically relevant fungal species. The use of these two primers in the PCR reaction produces amplification products having a length of approx. 500 base-pairs, and are thus easy to be further processed since they can be easily detected by gel electrophoresis. In this way there is an identical detection process for all pathogenic fungal species since it was found that the two primer sequences bind to the various fungal DNAs.

It is preferred if the polymerase chain reaction is carried out with the following cycle:

c1) denaturation for 0.3–1 min, preferably for 0.5 min, at 90–96° C., preferably at 94° C.;
c2) hybridization for 0.5–1.5 min, preferably for 1 min, at 58–64° C., preferably at 62° C.;
c3) extension for 1.5–2.5 min, preferably for 2 min, at 68–75° C., preferably at 72° C.

It is preferred if a denaturation step of 5–9 min, preferably 3 min, at 90–96° C., preferably 94° C., is carried out before the start of the cycle steps.

It was found that the PCR is very reproducible and above all highly specific under the aforementioned conditions so that it can be ensured that the amplification products are in fact segments of the original fungal DNA.

It is furthermore preferred if in step d) the amplification products are detected by gel electrophoresis, preferably on an agarose gel, and are preferably stained with ethidium bromide.

The advantage of this is that a known and well established detection method is used to show that amplification products which indicate a fungal infection are in fact produced by the PCR reaction.

It is further preferred if a DNA sequence from the fungal gene for the 18ssu-rRNA is amplified.

The inventor of the present application found that this fungal gene displays a specific sequence segment in the various fungal strains and species which on the one hand is flanked by two binding regions for primers which are identical for all fungal strains and species, though on the other hand the sequence of this segment differs to such an extent for the various fungal strains and species that it can be used to detect individual fungal species and strains.

The invention further relates to the nucleotide sequences SEQ ID-No: 1 and SEQ ID-No: 2 from the enclosed sequence listing. It is preferable if these two nucleotide sequences are used to amplify a segment of fungal DNA.

The invention also relates to a kit to detect fungal DNA in a test solution, and the kit contains primers for a polymerase chain reaction binding to the DNA of a number of fungal species. The kit preferably contains the nucleotide sequences SEQ ID-No: 1 and SEQ ID-No: 2 from the sequence listing as primers.

The invention also relates to a kit to carry out the process described above.

The advantage of such a kit is that all necessary solutions, and in particular the necessary primers, can be put together so that they can be used for routine procedures. Thus these new kits can be used in everyday laboratory work to detect fungal species in test solutions. Moreover, this kit can be used to amplify certain segments of the proven fungal species which can then be used for further identification processes, for example.

The object of the present application is also the third step of the process, either isolated or in combination with the first and the second steps of the process described above, i.e. the identification of the fungal species using the extracted and detected fungal DNA.

The fungal identification of the species should be able to be carried out quickly and easily for diagnostic purposes so that it can be employed in everyday work in hospitals by trained personnel.

This object is achieved in accordance with the invention inasmuch as the following step is carried out:
e) identification of the nucleotide sequence sections of the DNA contained in the test solution characterizing the fungal species.

Since the detection process is carried out on the DNA level it is sufficient if certain segments of the fungal DNA are identified provided these segments are specific for the respective fungal species. Standard methods can be used by sequencing at least a part of the amplification product, investigating the melting behavior of the double strands, etc.

These processes can generally be performed quickly and easily so that they can also be carried out by trained personnel.

It is preferred if the fungal DNA or segments of the fungal DNA are hybridized with DNA probes which are specific for defined fungal strains and/or species in step e), the test of successful hybridization leading to an identification of the fungal species.

The advantage of this is that a very fast and simple hybridization process is used for identification. Specific probes are used which are specific to the respective fungal species so that they bind exclusively to the amplified segments of these fungal species. Such processes can be carried out on gels, for example, the hybrids being shown by staining. A further process consists of exploiting the optically different behaviors of single strands and double-stranded regions, e.g. optical density, dichroism or similar features.

It is furthermore preferred if the probes are labeled with digoxigenin for testing of successful hybridization and if the hybrids are detected using the Southern-Blot method, for instance.

This step further simplifies the process, the probes themselves are already provided with the corresponding marker which shows the formation of hybrids following hybridization, preferably by visually detectable dye reactions, using a well-known method.

It is preferred if one or more of the nucleotide sequences SEQ ID-No: 3 to SEQ ID-No: 8 from the enclosed sequence listing are used as DNA probes, the DNA probes being preferably used sequentially in the sequence SEQ ID-No: 3, SEQ ID-No: 8, SEQ ID-No: 6, SEQ ID-No: 7, SEQ ID-No: 4 and SEQ ID-No: 5 and if the respective hybridization is tested.

The individual fungal species can be tested in the order of their frequency by the sequential hybridization, thus significantly accelerating the detection process.

The invention further relates to the nucleotide sequences SEQ ID-No: 3-SEQ ID-No: 8 from the enclosed sequence listing.

The invention further relates to the use of one or more of these nucleotide sequences as DNA probes to identify fungal species.

The advantage here is that the 6 specified nucleotide sequences can specifically discriminate between all clinically relevant fungal species.

The nucleotide sequence SEQ ID-No: 3 detects the fungal species *Candida albicans,* SEQ ID-No: 4 detects *Candida glabrata,* SEQ ID-No: 5 detects *Candida krusei,* SEQ ID-No: 6 detects *Candida tropicalis,* SEQ ID-No: 7 detects *Candida parapsilosis* and SEQ ID-No: 8 detects fungal species belonging to the strain Aspergillus, particularly *A. fumigatus, A. flavus, A. versicolor, A. niger, A. nidulans* and *A. terreus.*

The invention further relates to a kit to identify fungal species which contains DNA probes which hybridize to specific nucleotide sequence sections of the DNA of the respective fungal species. The kit preferably contains one or more of the nucleotide sequences SEQ ID-No: 3-SEQ ID-No: 8 from the enclosed sequence listing as DNA probes.

The invention further relates to a kit to carry out the process described above.

The advantage of this is that such a kit can be provided with either only the DNA probes or additionally with the adequate additional solutions so that all primary solutions, etc. necessary for everyday laboratory work can be taken directly from this kit. This considerably simplifies the detection or the identification of the respective fungal species since the individual primary solutions no longer have to be produced separately in the laboratory. However, it is also possible to include only the probes and possibly the primers and enzyme/primary solutions for the polymerase chain reaction in this kit so that apart from this, standard primary solutions can be used.

A process for detection of fungal cells in whole blood comprising the steps detailed above in an advantageous manner comprises the following steps:
isolation of predominantly intact fungal cells from whole blood,
extraction of DNA from the isolated fungal cells,
amplification of at least one segment of the isolated fungal DNA, preferably of at least one segment of the fungal gene for the 18ssu-rRNA,
detection of the amplification products according to a yes/no decision, and
assigning the amplification products to individual fungal species by hybridizing them with DNA probes being specific for defined fungal strains and/or species.

One of the main advantages of this summarized process is that only one amplification step is required amplifying a segment of the fungal DNA, preferably a segment of the fungal gene for the 18ssu-rRNA in such a way that the amplification products can be used for the yes/nor decision as well for the determination of the fungal species. The inventor of the present application has found that the fungal gene for the 18ssu-rRNA can at least partly be flanked by two primers being identical for all fungal species of interest on the one hand, the amplicon being different for the various fungal species on the other hand, so that it can be hybridized with different probes characteristic for the fungal species.

A single amplification step therefore is sufficient to answer the question whether there is a fungal infection at all and to answer the question which fungal species is concerned. The process is therefore extremely simple and can be easily carried out, specialized knowledge is not required, so that it can be carried out even by trained personnel.

Further advantages can be taken from the following description.

It is understood that the aforementioned features and those to be explained in the following can be used not only in the specified combinations but also in other combinations or alone without going beyond the scope of the present invention.

Examples of the performance of the individual procedural steps and the use of the process within the scope of a program of a clinical test program are quoted in the following description.

A particular advantage of the new process is the fact that it is performed using whole blood, i.e. no biopsy is required and no serum which first has to be produced is used. The fungal cells are firstly separated from the cellular DNA in the whole blood. This is necessary for the fungal DNA, which may only be present in very small quantities, not having to be detected against the background of the much higher concentration of cellular DNA. This also increases the specificity of the detection process. For this purpose the erythrocytes are initially lysed by osmotic hemolysis and the leukocytes are then enzymatically digested. These two procedural steps are selected in such a way that the fungal cells themselves are not yet damaged and that any phagocyted fungal cells are released undamaged so that they are also available for subsequent detection.

EXAMPLE 1

Lysis of Erythrocytes by Osmotic Hemolysis

The lysis of the erythrocytes is carried out using a hypotonic solution. The following buffer having the following final concentration is used:

| | |
|---|---|
| Tris pH 7.6 | 10 mM |
| $MgCl_2$ | 5 mM |
| NaCl | 10 mM |

The solution is incubated for 10 min at room temperature and then centrifuged.

An amount of 3 ml whole blood is sufficient for the first step.

EXAMPLE 2

Enzymatic Digestion of Leukocytes

The leukocytes, which may contain fungal cells, are carefully disintegrated by enzymatically digesting the cells with proteinase K (20 µg/ml) obtained from Boehringer Mannheim, in the following buffer containing the following final concentrations, in which the pellet from example 1 is resuspended:

| | |
|---|---|
| Tris pH 7.6 | 10 mM |
| EDTA pH 8.0 | 10 mM |
| NaCl | 50 mM |
| SDS | 0.2% |
| Proteinase K | 200 µg/ml |

This buffer is incubated for two hours at 65° C.

EXAMPLE 3

Separation of Predominantly Intact Fungal Cells, Above All from Cellular DNA

Once the blood cells have been disintegrated the way explained in examples 1 and 2, so that the cellular DNA has been released, centrifugation is carried out at 5000 rpm, leading to a considerable loss of cellular DNA since DNA does not sediment at this centrifugation speed.

The sediment now contains all free or released fungal cells which are resuspended in a buffer (Aqua bidest) for further processing.

EXAMPLE 4

Disintegration of the Fungal Cells

The fungal cells are now lysed in alkaline and enzymatically treated to release the fungal DNA.

Firstly an alkaline lysis is carried out using 200 ml 50 mM NaOH for 10 min at 95° C.

This step is followed by a neutralization step using 1 M Tris-HCl pH 7.0.

500 µl Zymolyase from Sigma (300 µg/ml) are then added and the solution is incubated for 60 min at 37° C. to enzymatically digest the fungal cells.

500 µl Tris/EDTA and 50 ml 10% SDS solution are then added and the solution is incubated at 65° C. for 20 min to denature the protein.

EXAMPLE 5

Isolation of Fungal DNA

Fungal cell debris and free fungal DNA, which has next to be isolated, are present in this solution.

Firstly a protein precipitation is carried out using 5 M potassium acetate, after which the supernatant is removed and the DNA precipitated by adding ice-cold isopropanol. The precipitation product is then used for the further procedural steps.

The procedural steps specified in examples 1–5 permit the extraction of fungal DNA in a highly selective way from whole blood which is then available as a precipitate and is only slightly contaminated with cellular DNA, so that the following detection can be carried out in a very sensitive way and with a high specificity.

EXAMPLE 6

Amplification of a Fungus Specific DNA Segment

In this procedural step it will initially be shown whether fungal DNA is at all present in the precipitate obtained from the procedural step of example 5. This step makes use of the fact that the DNA sequences shown in the sequence listing as SEQ ID-No: 1 and SEQ ID-No.: 2 bind specifically to binding sites on the fungal gene for the 18ssu-rRNA of numerous fungal strains and species.

The inventor of the present application has found that this fungal gene in the various fungal strains and species displays a specific sequence segment which on the one hand is flanked by two binding regions for primers which are identical for all fungal strains and species, though on the other hand the sequence of this segment differs to such an extent for the various fungal strains and species that it can be used to detect individual fungal species and strains.

The DNA sequence SEQ ID-No: 1 binds to the sense strand, whereas the DNA sequence SEQ ID-No: 2 binds to the anti-sense strand, the distance between the two binding sites being approx. 500 base-pairs. These two DNA sequences SEQ ID-No: 1 and SEQ ID-No: 2 are thus suitable as primers for a polymerase chain reaction (PCR), which results in the production of amplification products (amplicon) with a length of approx. 500 base-pairs.

The position of the primers and length of the respective amplicon are shown in the following Table 1.

TABLE 1

Amplicons obtained from fungal pathogens

| Fungal species | Binding sites of primers | | Length of amplicon |
|---|---|---|---|
| | Forward primer | Reverse primer | |
| C. albicans | bp544-563 | bp1033-1014 | bp490 |
| C. glabrata | bp546-565 | bp1047-1028 | bp502 |
| C. krusei | bp535-554 | bp1016-997 | bp482 |
| C. tropicalis | bp544-563 | bp1030-1011 | bp487 |
| C. parapsilosis | bp544-563 | bp1033-1014 | bp490 |
| A. fumigatus | bp544-563 | bp1046-1027 | bp503 |
| A. niger | bp483-502 | bp986-967 | bp503 |
| A. flavus | bp483-502 | bp985-966 | bp502 |
| A. terreus | bp481-500 | bp984-965 | bp503 |
| A. nidulans | bp581-500 | bp984-965 | bp503 |

Using the two primers SEQ ID-No: 1 and SEQ ID-No: 2 the production of sufficient amounts of amplicons of approx. 500 base-pairs for all relevant fungal species of the Candida and Aspergillus strains in the PCR procedure can be obtained.

The PCR conditions are as follows:

Buffer (50 µl):

10 mM Tris pH 9.6
50 mM NaCl
10 mN MgCl$_2$
0.2 mg/ml BSA
Polymerase
each 0.5 mM nucleotide
each 100 pM primer
Initial denaturation:      3 min at 94° C.
Cycle denaturation:        0.5 min at 94° C.
Annealing:                 1 min at 62° C.
Extension:                 2 min at 72° C.
Terminal extension:        5 min at 72° C.
Number of cycles:          34

The high magnesium concentration in the buffer permits a high specificity of the polymerase which can work at its optimum temperature of 72° C in the extension step.

A total of 40 strains of Candida albicans, 10 *Candida tropicalis*, 6 *Candida parapsilosis*, 11 *Candida glabrata*, 8 *Candida krusei*, 8 *Aspergillus fumigatus*, 6 *Aspergillus flavus*, 5 *Aspergillus terreus*, 7 *Aspergillus niger*, 5 *Aspergillus nidulans* and 3 *Aspergillus versiculor* could be successfully amplified with these primers.

EXAMPLE 7

Detection of Amplification Products from Example 6

In the next step it is shown whether DNA segments with a length of approx. 500 base pairs are actually amplified during the PCR reaction in example 6. The detection of the fungus specific DNA segments is carried out by ethidium bromide staining of the specific bands in a 2% agarose gel.

If the specific band is detected here a fungal infection can be assumed since the primers SEQ ID-No: 1 and SEQ ID-No: 2 bind to all the aforementioned fungal strains. Thus, if fungal DNA is extracted during the procedural steps of examples 1–5, it is amplified by the PCR step of example 6 to such an extent that it can be detected by ethidium bromide staining.

EXAMPLE 8

Classification of the Amplification Products from Example 6 in Individual Fungal Species The fungal infection already proven in step 7 next has to be specified more precisely for a specific therapy. A further advantage of the PCR step from example 6 now becomes apparent. Enough fungus-specific DNA segments have been produced for further detection methods for a determination of the fungal species.

The nucleotide sequences SEQ ID-No: 3 to SEQ ID-No: 8 specified in the sequence listing are used here; these serve as species-specific probes which hybridize specifically with a sequence section of the DNA segment produced in example 6.

It has been found that probe SEQ ID-No: 3 hybridizes with *Candida albicans*, SEQ ID-No: 4 with *Candida glabrata*, SEQ ID-No: 5 with *Candida krusei*, SEQ ID-No: 6 with *Candida tropicalis*, SEQ ID-No: 7 with *Candida parapsilosis* and SEQ ID-No: 8 with *Aspergillus fumigatus, A. flavus, A. versiculor, A. niger, A. nidulans* and *A. terreus*. The nucleotide sequence SEQ ID-No: 8 is thus a general Aspergillus probe whereas the nucleotide sequences SEQ ID-No: 3-SEQ ID-No: 5 can discriminate between fungal species of the Candida strain.

In order to be able to prove the successful hybridization, the probes are labeled with the Transferase kit from Boehringer Mannheim, the detection being carried out according to the Southern-Blot method using the known color reactions.

A sequential hybridization is carried out with these probes which is graduated according to the frequency of the individual fungal species so that hybridization starts with SEQ ID-No: 3 (*C. albicans*), then SEQ ID-No: 8 (Aspergillus), SEQ ID-No: 6 (*C. tropicalis*), SEQ ID-No.: 7 (*C. parapsilosis*), SEQ ID-No.: 4 (*C. glabrata*) and finally SEQ ID-No.: 5 (*C. krusei*).

In this way it is possible to identify the fungal species according to the amplification products produced in step example 6 and to then initiate a specific therapy.

EXAMPLE 9

Detection of Fungal Cells Disseminated in Blood

With the aid of specific amplification and sequential hybridization it was possible to successfully detect fungal species with a sensitivity of 1–3 fungal cells. Through a dissemination of fungal species in blood samples it could be proven that the aforementioned process reaches a sensitivity of one so-called CFU (colony forming unit)/ml blood. This detection limit is far below that which can be expected for a clinically relevant fungal dissemination in blood.

EXAMPLE 10

Program of Clinical Tests

In a large-scale program of clinical tests a high specificity of the new process could be shown during the analysis of 165 blood samples from 65 healthy test persons. All 165 blood samples remained negative.

94 immunosuppressed patients with unclear fever were then tested for the presence of a fungal infection. Of 65 patients having no invasive fungal infection, over 200 blood samples (apart from one exception) were also negative.

On the other hand, all 25 patients having an invasive fungal infection could be identified to be positive already within the first week. Moreover, the causative fungal pathogen could be classified for all patients.

What is claimed is:

1. A method for detection of fungal DNA in clinical material comprising:
   a) isolating predominantly intact fungal cells from whole blood by disintegrating blood cells and isolating intact fungal cells;
   b) isolating fungal DNA from the intact fungal cells by disintegrating the intact fungal cells and isolating the fungal DNA; and
   c) amplifying at least one segment of the fungal DNA to be detected by polymerase chain reaction, wherein at least one of the nucleotide sequences SEQ ID-No: 1 or SEQ ID-No: 2 are used as a primer.

2. The method of claim 1, further comprising detecting amplification products.

3. The method of claim 2, wherein detecting amplification products comprises gel electrophoresis and staining the gel.

4. The method of claim 3, wherein said gel electrophoresis comprises an agarose gel and wherein ethidium bromide is used to stain said gel.

5. The method of claim 1, wherein the polymerase chain reaction is carried out with a cycle as follows:
   denaturing for 0.3–1 min at 90–96° C.
   hybridizing for 0.5–1.5 min at 58–64° C., and
   extending for 1.5–2.5 min at 63–75° C.

6. The method of claim 5, wherein denaturing is for 0.5 min at 94° C., wherein hybridizing is for 1 min at 62° C., and wherein extending is for 2 min at 72° C.

7. The method of claim 5, further comprising an initial denaturation step of 5–9 min at 90–96° C. before the start of the cycle.

8. The method of claim 7, wherein the initial denaturation step is for 3 min at 94° C.

9. The method of claim 1, wherein said at least one segment of fungal DNA amplified in step c) comprises a segment of a fungal gene for 18ssu-rRNA.

10. The method of claim 9, wherein SEQ ID-No: 1 is used as a primer for the polymerase chain reaction.

11. The method of claim 9, wherein SEQ ID-No: 2 is used as a primer for the polymerase chain reaction.

12. The method of claim 1, wherein isolating predominantly intact fungal cells from whole blood by disintegrating blood cells and isolating intact fungal cells, further comprises:
   forming a blood cell lysate by disintegrating erythrocytes by osmotic hemolysis and disintegrating leukocytes by enzymatic digestion; and
   centrifuging the resultant blood cell lysate to isolate the intact fungal cells from blood cell lysate.

13. The method of claim 12, wherein forming a blood cell lysate is carried out in a solution with a final concentration of 200 µg/ml of proteinase K, 10 mM Tris pH 7.6, 10 mM EDTA pH 8.0, 50 mM NaCl and 0.2% SDS.

14. The method of claim 13, wherein said solution is incubated for 100–140 min at 60–70° C.

15. The method of claim 13, wherein said solution is incubated for 120 min at 65° C.

16. The method of claim 12, wherein disintegrating erythrocytes by osmotic hemolysis comprises incubation in a hypotonic solution and a detergent at a final concentration of 10 mM Tris pH 7.6, 5 mM $MgCl_2$ and 10 mM NaCl.

17. The method of claim 1, wherein isolating fungal DNA from the intact fungal cells by disintegrating the intact fungal cells and isolating the fungal DNA, comprises alkaline lysis and enzymatic treatment of the intact fungal cells.

18. The method of claim 1, wherein isolating fungal DNA from the intact fungal cells by disintegrating the intact fungal cells and isolating the fungal DNA, comprises:
   incubating the fungal cells for 5–15 min at 90–95° C. in a solution with 50 mM NaOH;
   neutralizing with 1 M Tris-HCl pH 7.0;
   treating with Zymolyase enzyme for 50–70 min at 30–40° C.; and
   denaturing protein by incubating with Tris/EDTA for 10–30 min at 60–70° C.

19. The method of claim 18, wherein incubating the fungal cells is for 10 min at 95° C., wherein treating with Zymolyase is for 60 min at 37° C., and wherein incubating with Tris/EDTA is for 20 min at 65° C.

20. The method of claim 1, wherein isolating fungal DNA from the intact fungal cells by disintegrating the intact fungal cells and isolating the fungal DNA, comprises
   precipitating protein with 5M potassium acetate; and
   precipitating DNA in ice-cold isopropanol.

21. The method of claim 1, further comprising:
   d) determining whether the nucleotide sequence of said at least one segment of fungal DNA is characteristic of a particular fungal strain and/or species, wherein said at least one segment of fungal DNA is hybridized with DNA probes specific for the particular fungal strain and/or species, said DNA probes being selected from the group consisting of SEQ ID-No: 3, SEQ ID-No: 4; SEQ ID-No: 5, SEQ ID-No-6, SEQ ID-No: 7 and SEQ ID-No: 8, and wherein a successful hybridization leads to identification of the fungal strain and/or species.

22. The method of claim 21, wherein the probes are labeled with dioxygenin and hybrids are detected for testing of successful hybridization.

23. The method according to claim 22, wherein detection of hybrids is by Southern-Blot analysis.

24. The method according to claim 21, wherein the DNA probes are used in the following sequential order SEQ ID-No: 3, SEQ ID-No: 8, SEQ ID-No: 6, SEQ ID-No: 7, SEQ ID-No: 4, and SEQ ID-No: 5, and wherein the hybridization is tested respectively.

25. A method for detection of fungal DNA in clinical material comprising:
   a) isolating predominantly intact fungal cells from whole blood by disintegrating blood cells by osmotic hemolysis and enzymatic digestion, and isolating intact fungal cells;
   b) isolating fungal DNA from the intact fungal cells by disintegrating the intact fungal cells by alkaline lysis and enzymatic treatment and isolating the fungal DNA;
   c) amplifying at least one segment of the fungal DNA to be detected by polymerase chain reaction;

d) determining whether the nucleotide sequence of said at least one segment of fungal DNA is characteristic of a particular fungal strain and/or species, wherein said at least one segment of fungal DNA is hybridized with DNA probes specific for the particular fungal strain and/or species, said DNA probes being selected from the group consisting of SEQ ID-No: 3, SEQ ID-No: 4; SEQ ID-No: 5, SEQ ID-No-6, SEQ ID-No: 7 and SEQ ID-No: 8, and wherein a successful hybridization leads to identification of the fungal strain and/or species.

26. The method of claim 25, wherein said at least one segment of fungal DNA amplified in step c) comprises a segment of a fungal gene for 18ssu-rRNA.

27. A method for detection of fungal DNA in clinical material comprising:
   a) isolating predominantly intact fungal cells from whole blood by disintegrating blood cells by osmotic hemolysis and enzymatic digestion, and isolating intact fungal cells;
   b) isolating fungal DNA from the intact fungal cells by disintegrating the intact fungal cells by alkaline lysis and enzymatic treatment and isolating the fungal DNA;
   c) amplifying at least one segment of the fungal DNA to be detected by polymerase chain reaction using at least one primer;
   d) determining whether the nucleotide sequence of said at least one segment of fungal DNA is characteristic of a particular fungal strain and/or species, wherein said at least one segment of fungal DNA is hybridized with DNA probes specific for the particular fungal strain and/or species, and wherein a successful hybridization leads to identification of the fungal strain and/or species.

28. The method of claim 27, wherein the at least one primer in step c) is selected from the group consisting of SEQ ID-No: 1 and SEQ ID-No: 2.

29. The method of claim 27, wherein the DNA probes in step d) are selected from the group consisting of SEQ ID-No: 3, SEQ ID-No: 4, SEQ ID-No: 5, SEQ ID-No: 6, SEQ ID-No: 7 and SEQ ID-No: 8.

30. A method for detection of fungal DNA in clinical material comprising:
   a) isolating predominantly intact fungal cells from whole blood by disintegrating blood cells and isolating intact fungal cells;
   b) isolating fungal DNA from the intact fungal cells by disintegrating the intact fungal cells and isolating the fungal DNA;
   c) amplifying at least one segment of the fungal DNA to be detected by polymerase chain reaction using at least one primer; and
   d) determining whether the nucleotide sequence of said at least one segment of fungal DNA is characteristic of a particular fungal strain and/or species, wherein said at least one segment of fungal DNA is hybridized with DNA probes specific for the particular fungal strain and/or species, and wherein a successful hybridization leads to identification of the fungal strain and/or species.

31. The method of claim 30, wherein the at least one primer in step c) is selected from the group consisting of SEQ ID-No: 1 and SEQ ID-No: 2.

32. The method of claim 30, wherein the DNA probes in step d) are selected from the group consisting of SEQ ID-No: 3, SEQ ID-No: 4, SEQ ID-No: 5, SEQ ID-No: 6, SEQ ID-No: 7 and SEQ ID-No: 8.

* * * * *

UNITED STATES PATENT AND TRADEMARK OFFICE
CERTIFICATE OF CORRECTION

PATENT NO. : 6,605,439 B2
DATED : August 12, 2003
INVENTOR(S) : Hermann Einsele

It is certified that error appears in the above-identified patent and that said Letters Patent is hereby corrected as shown below:

Title page,
Item [63], Foreign Application Priority Data, should read as follows:
-- Continuation of application No. 09/011,930, filed on June 22, 1998, now abandoned. --

Signed and Sealed this

Nineteenth Day of April, 2005

JON W. DUDAS
*Director of the United States Patent and Trademark Office*

```
                          SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "DNA"

(iii) HYPOTHETICAL: YES (xi) SEQUENCE DESCRIPTION: SEQ ID NO: 1:

ATTGGAGGGC AAGTCTGGTG                                             20

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "DNA"

(iii) HYPOTHETICAL: YES (xi) SEQUENCE DESCRIPTION: SEQ ID NO: 2:

CCGATCCCTA GTCGGCATAG                                             20

(2) INFORMATION FOR SEQ ID NO: 3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "DNA"

(iii) HYPOTHETICAL: YES (xi) SEQUENCE DESCRIPTION: SEQ ID NO: 3:

TCTGGGTAGC CATTTATGGC GAACCAGGAC                                  30

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

(ii) MOLECULE TYPE: other nucleic acid
            (A) DESCRIPTION:    /desc = "DNA"

(iii) HYPOTHETICAL: YES (xi) SEQUENCE DESCRIPTION: SEQ ID NO: 4:

TTCTGGCTAA CCCCAAGTCC TTGTGGCTTG                                    30

(2) INFORMATION FOR SEQ ID NO: 5:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "DNA"

(iii) HYPOTHETICAL: YES (xi) SEQUENCE DESCRIPTION: SEQ ID NO: 5:

GTCTTTCCTT CTGGCTAGCC TCGGGCGAAC                                    30

(2) INFORMATION FOR SEQ ID NO: 6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "DNA"

(iii) HYPOTHETICAL: YES (xi) SEQUENCE DESCRIPTION: SEQ ID NO: 6:

GTTGGCCGGT CCATCTTTCT GATGCGTACT                                    30

(2) INFORMATION FOR SEQ ID NO: 7:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "DNA"

(iii) HYPOTHETICAL: YES (xi) SEQUENCE DESCRIPTION: SEQ ID NO: 7:

TTTCCTTCTG GCTAGCCTTT TTGGCGAACC                                    30

(2) INFORMATION FOR SEQ ID NO: 8:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION:    /desc = "DNA"

(iii) HYPOTHETICAL: YES

-continued (xi) SEQUENCE DESCRIPTION: SEQ ID NO: 8:

CATGGCCTTC ACTGGCTGTG GGGGGAACCA  30